(12) United States Patent
Gueret

(10) Patent No.: US 7,955,016 B2
(45) Date of Patent: Jun. 7, 2011

(54) COSMETIC OR DERMATOLOGICAL TREATMENT METHOD AND DEVICES FOR APPLICATION OF SUCH A METHOD

(75) Inventor: Jean-Louis H. Gueret, Paris (FR)

(73) Assignee: L'Oreal, Paris (FR)

( * ) Notice: Subject to any disclaimer, the term of this patent is extended or adjusted under 35 U.S.C. 154(b) by 1204 days.

(21) Appl. No.: 11/609,198

(22) Filed: Dec. 11, 2006

(65) Prior Publication Data

US 2007/0206986 A1    Sep. 6, 2007

Related U.S. Application Data

(60) Provisional application No. 60/754,282, filed on Dec. 29, 2005.

(30) Foreign Application Priority Data

Dec. 9, 2005  (FR) ...................................... 05 53822

(51) Int. Cl.
*A46B 11/00* (2006.01)
(52) U.S. Cl. ........................................ 401/125; 401/123
(58) Field of Classification Search .................. 401/1, 2, 401/118, 123, 125, 196, 261, 263, 265, 266
See application file for complete search history.

(56) References Cited

U.S. PATENT DOCUMENTS

| | | |
|---|---|---|
| 3,752,155 A | 8/1973 | Blinoff, Jr. et al. |
| 4,291,685 A | 9/1981 | Taelman |
| 5,615,962 A * | 4/1997 | Staub ............................ 401/173 |
| 5,775,344 A | 7/1998 | Clay |
| 5,856,653 A | 1/1999 | Boudreaux |
| 6,247,862 B1 * | 6/2001 | Garza ............................... 401/6 |
| 2003/0100936 A1 | 5/2003 | Altshuler et al. |
| 2005/0220828 A1 | 10/2005 | Ullom et al. |

FOREIGN PATENT DOCUMENTS

| | | |
|---|---|---|
| EP | 0 779 043 | 6/1997 |
| EP | 1 334 921 | 8/2003 |
| EP | 1 462 025 | 9/2004 |
| EP | 1 593 319 | 11/2005 |
| FR | 2 849 753 | 7/2004 |
| WO | WO 2004/062424 | 7/2004 |
| WO | WO 2005/087043 | 9/2005 |

OTHER PUBLICATIONS

U.S. Appl. No. 11/609,247, filed Dec. 11, 2006, Gueret.

* cited by examiner

*Primary Examiner* — David J Walczak
(74) *Attorney, Agent, or Firm* — Oblon, Spivak, McClelland, Maier & Neustadt, L.L.P.

(57) ABSTRACT

A device includes an assembly including a non-rotatable applicator. The applicator includes an application surface configured to treat an area of the human body such as the skin. The applicator further includes at least one material with thermal properties such that, when the at least one material is heated to a temperature above 30° C. and which temperature does not cause thermal damage to the skin when the application surface is contacted with the skin for 15 seconds, the application surface maintains, after this application, a temperature above or equal to 30° C. The applicator can include a grasping surface and a cavity with a compound inside. The applicator can typically be configured to withstand repeated heating, especially by microwave oven.

63 Claims, 11 Drawing Sheets

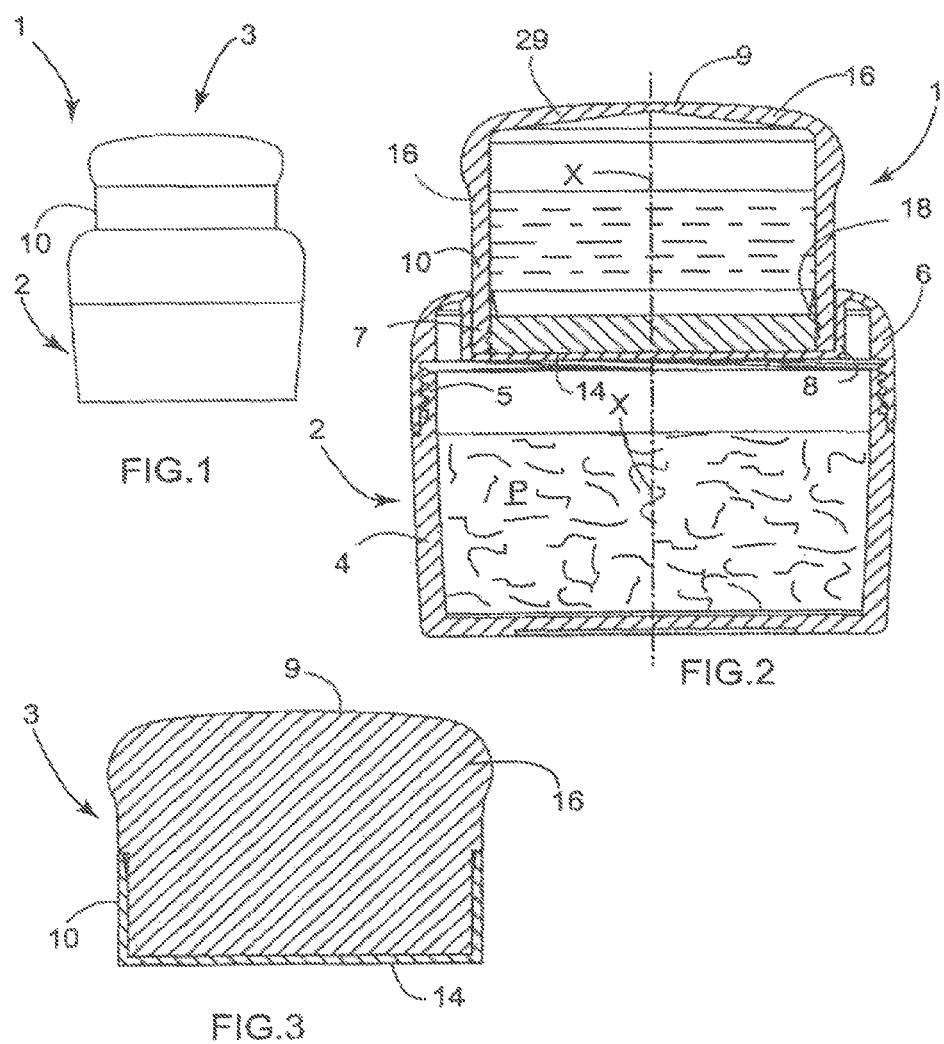

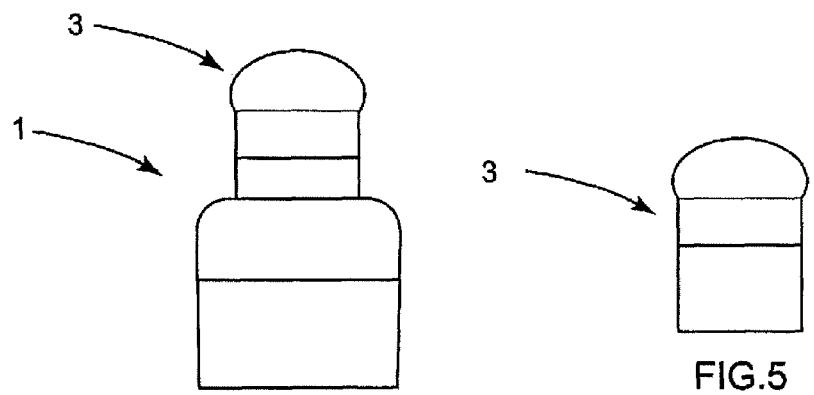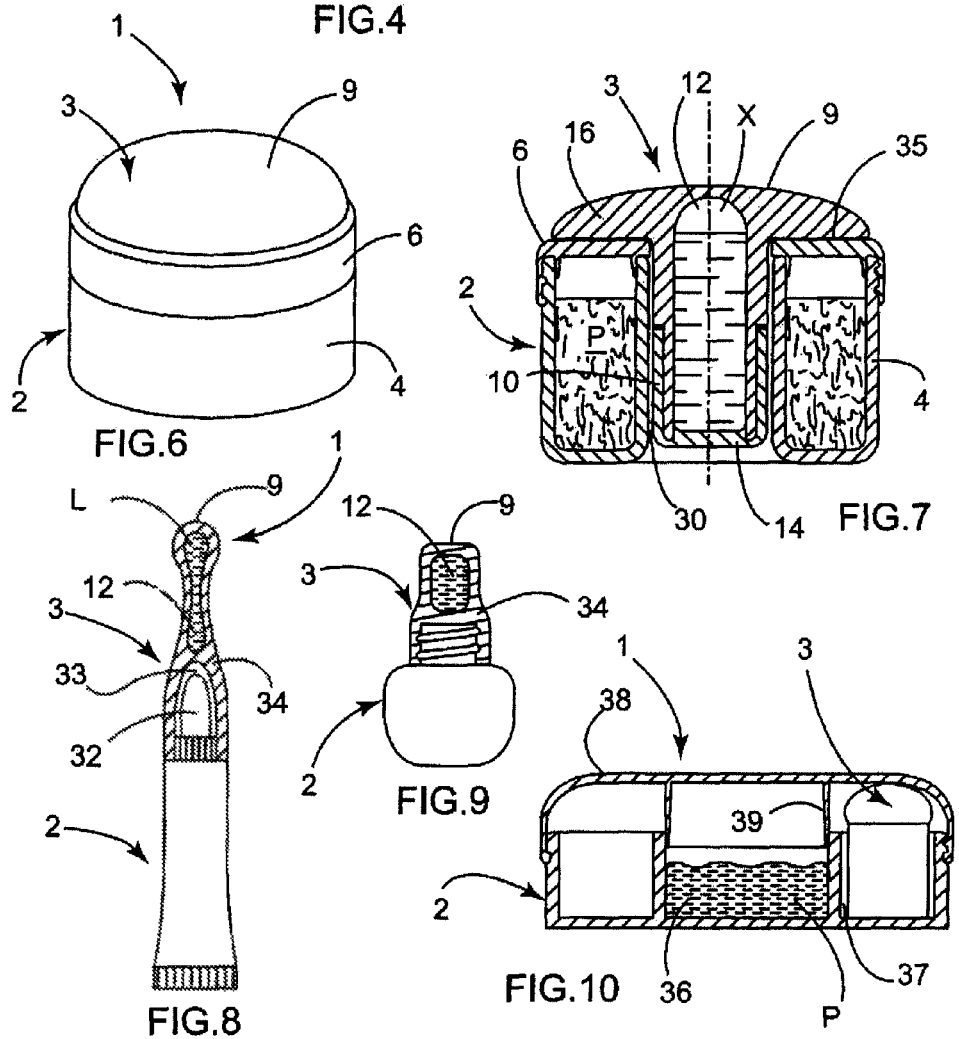

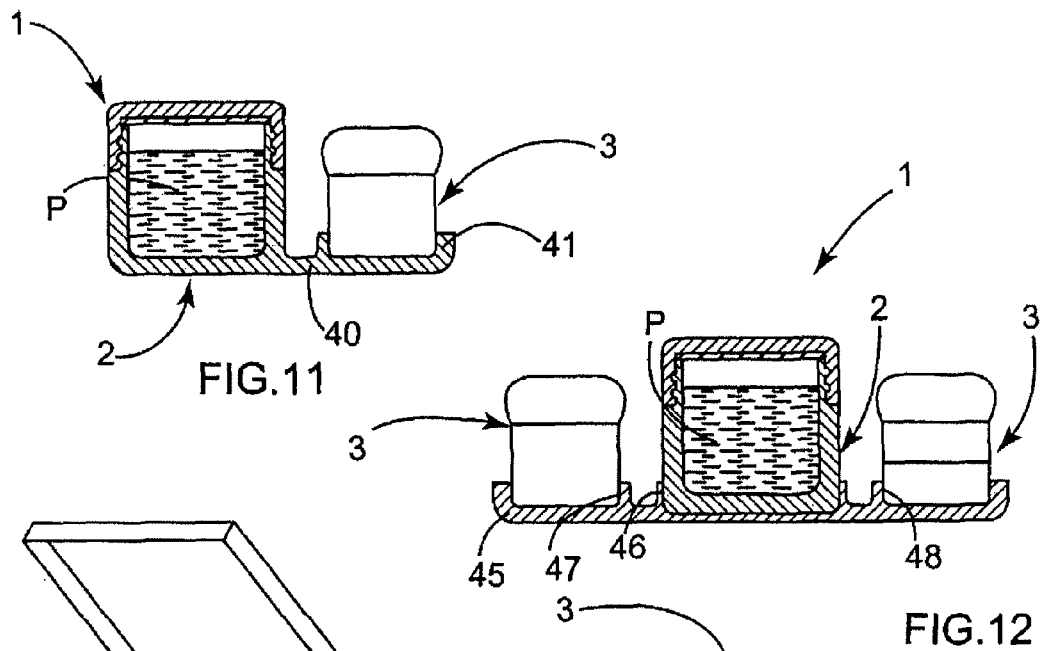
FIG.11
FIG.12
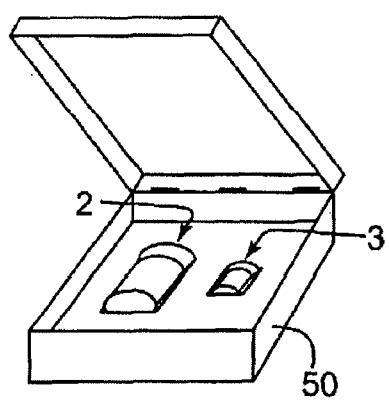
FIG.13
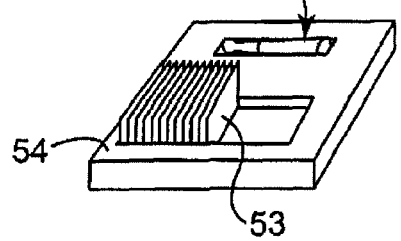
FIG.14
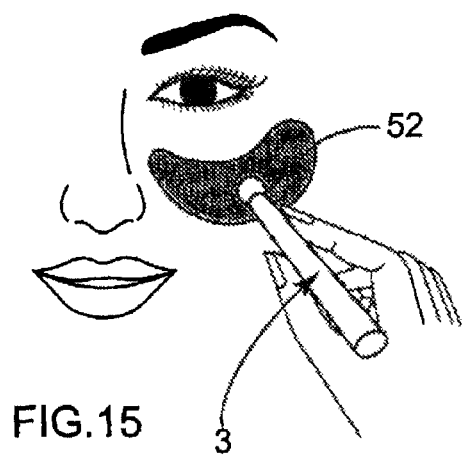
FIG.15

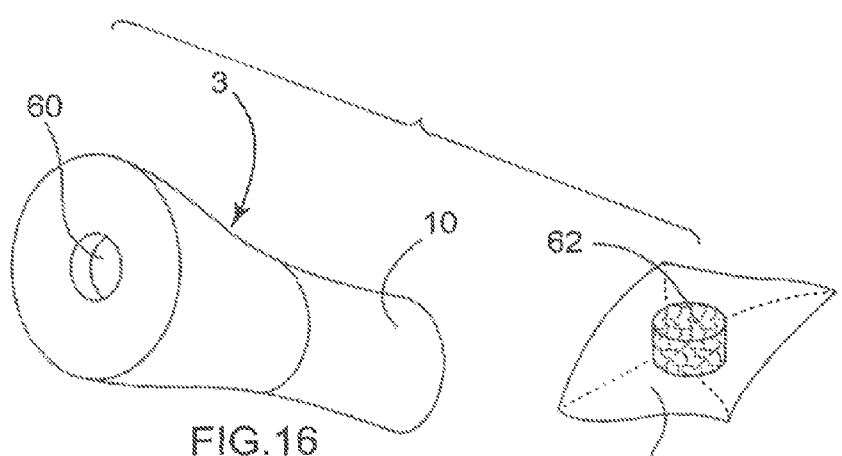
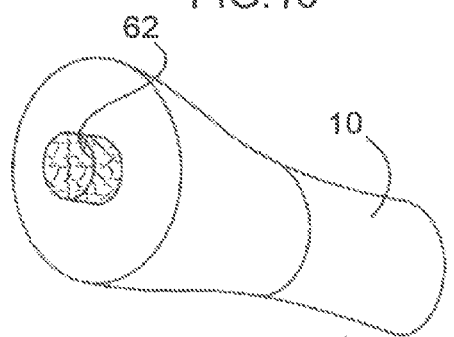
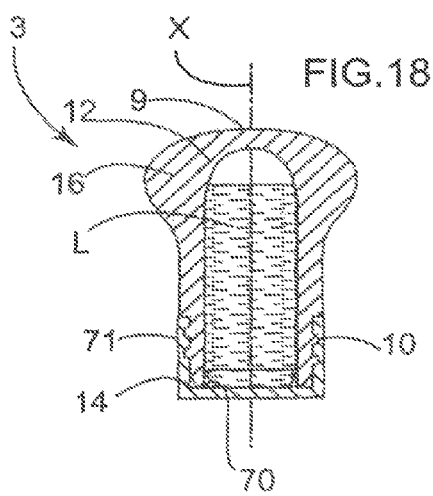
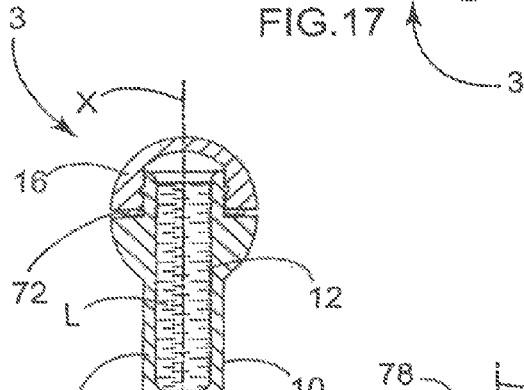
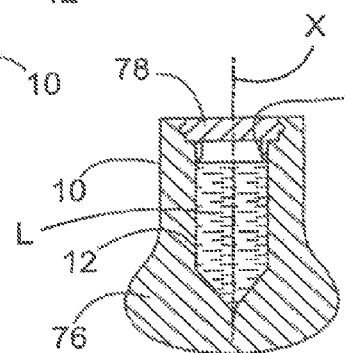
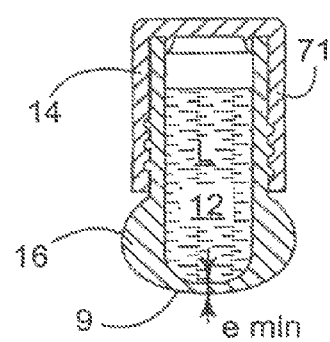

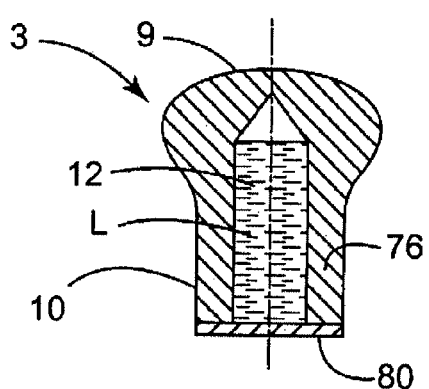
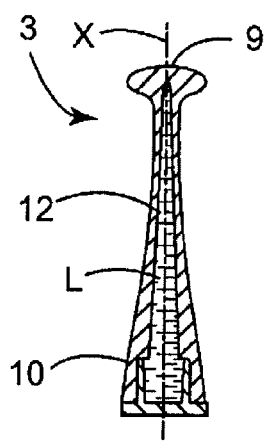
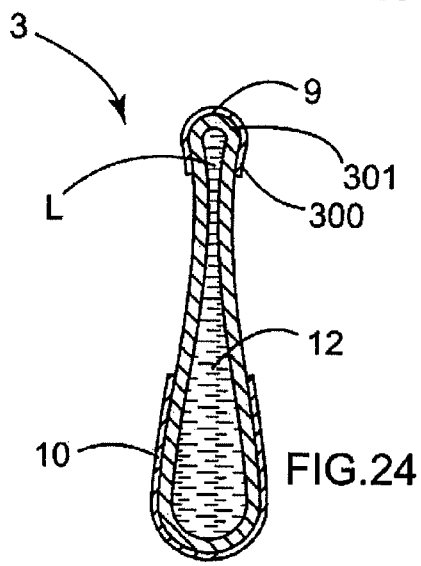
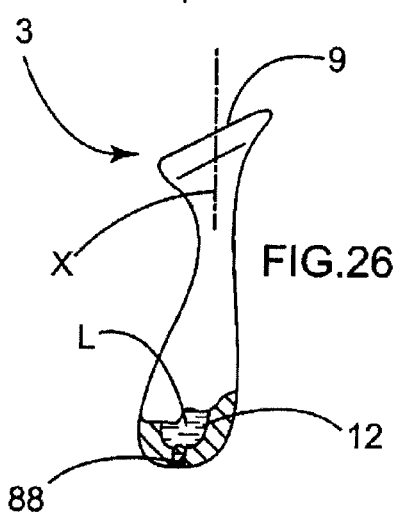
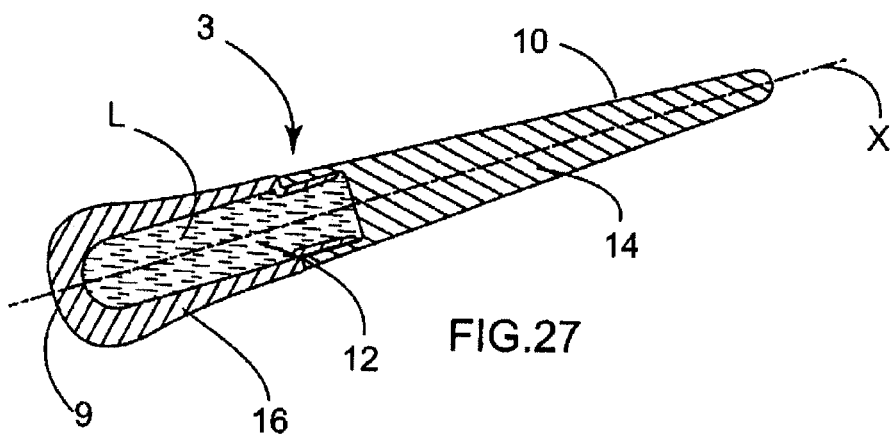

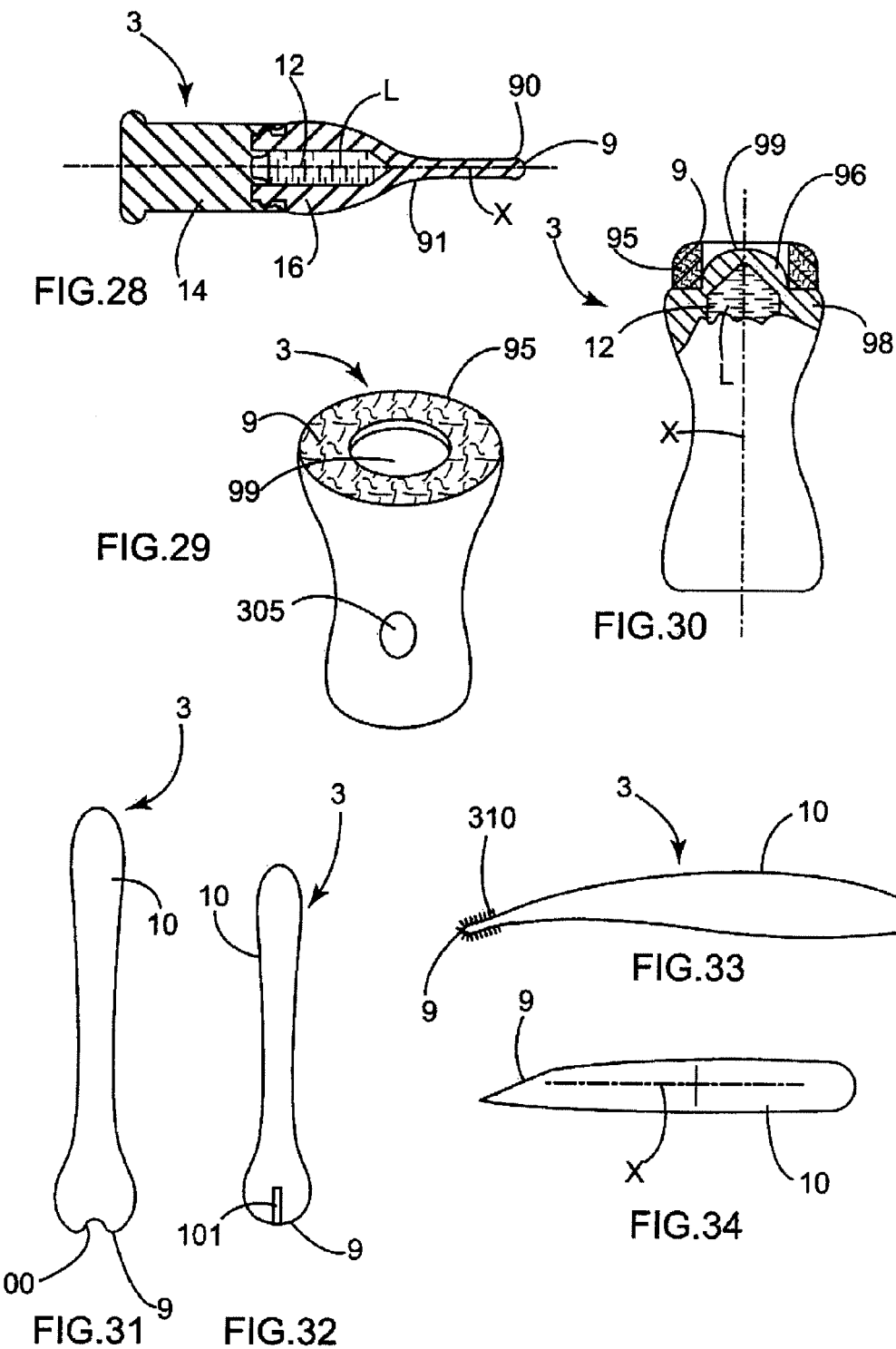

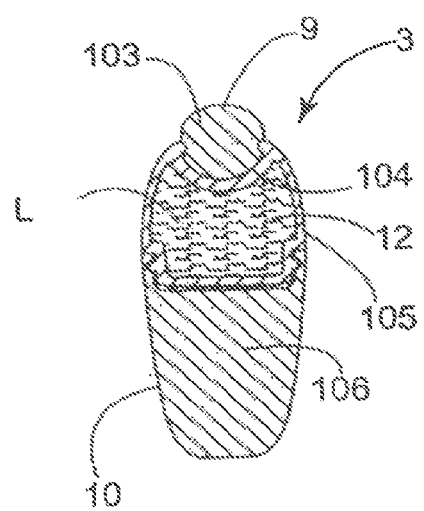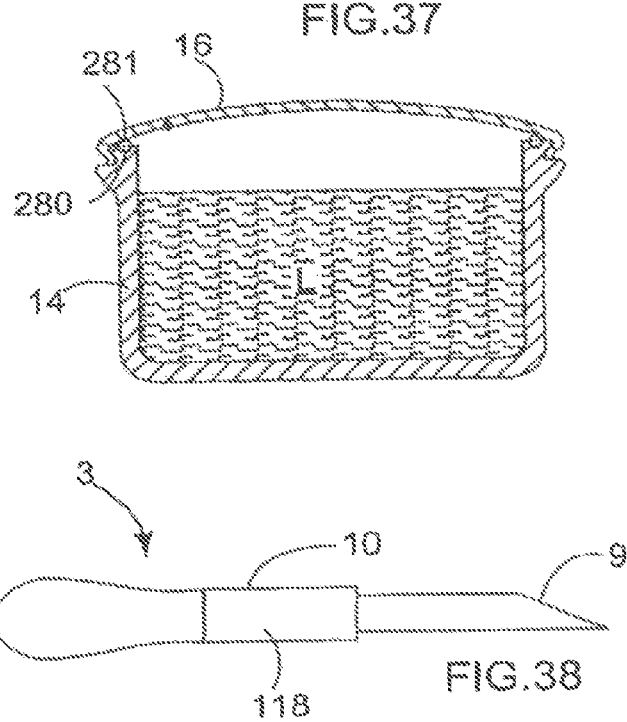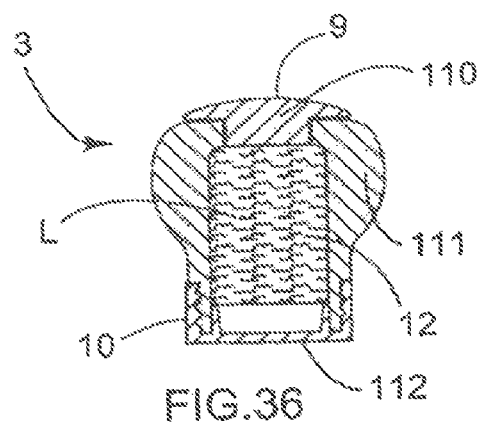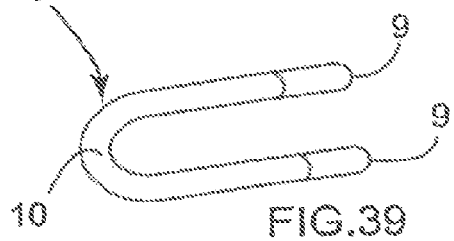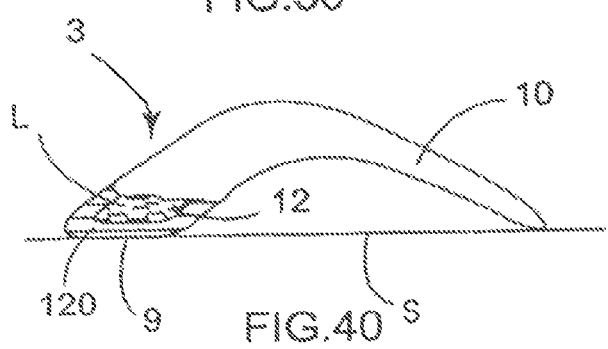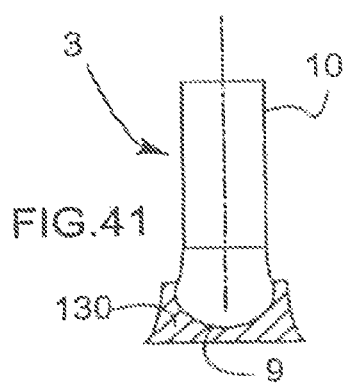

COSMETIC OR DERMATOLOGICAL TREATMENT METHOD AND DEVICES FOR APPLICATION OF SUCH A METHOD

CROSS-REFERENCE TO RELATED APPLICATIONS

This document claims priority to French Application Number 05 53822, filed Dec. 9, 2005, and U.S. Provisional Application No. 60/754,282, filed Dec. 29, 2005, the entire content of each of which are hereby incorporated by reference herein.

FIELD OF THE INVENTION

The present invention relates to the cosmetic or dermatological treatment of the skin with the application of heat, or the treatment of other keratinous materials such as the hair, for example.

BACKGROUND OF THE INVENTION

Discussion of Background

European Patent Application EP 1 593 319 describes a cosmetic treatment method in which a container is placed in a microwave oven to raise the temperature of a cosmetic composition contained inside. The composition heated in this way is applied by means of an applicator. French Application FR 2 849 753 describes a cosmetic treatment method in which a support impregnated with a cosmetic composition is placed in a microwave oven to raise the temperature of the cosmetic composition.

Furthermore, masks designed to be placed in a microwave oven so as to facilitate application of heat on the face are available. One such mask is marketed under the brand name COLDHOT® by the company 3M, and it can be used in a hot mode to improve the effectiveness of certain cosmetic products. However, the placement of cosmetic compositions in a microwave oven before application can pose certain formulation problems. In fact, certain cosmetic compositions are liable to deteriorate when heated, being unstable with respect to heat. Furthermore, when a small quantity of composition is used locally, the heat effect is of short duration due to cooling of the composition in contact with the air and the skin. Moreover, certain dispensing devices are designed to operate with compositions having particular rheological properties and may no longer work properly when the viscosity of the composition is modified following a change of temperature.

U.S. Pat. No. 3,752,155 describes a metal ball designed to be heated by an apparatus comprising heating resistances to the contact of which the ball is brought. U.S. Patent Pub. 2003/0100936 describes a roller into which can be introduced a heated liquid. PCT Patent Application No. WO 2005/087043 describes a method of treating keratinous tissues in which a sachet containing a composition is heated in a receptacle equipped with heating means. The sachet is in particular built from plastic films designed to be metallized.

European patent application EP 1 462 025 describes a mascara brush associated with a reservoir of product comprising a heating wall to heat the brush charged with product. U.S. Pat. No. 5,775,344 describes a mascara brush comprising a heating stem. U.S. Pat. No. 5,856,653 describes a heating container into which can be introduced a container containing a cosmetic product in order to heat it. The heating container comprises heating means which heat a fluid provided in the wall of the heating container. This is a desire to be able to enjoy the benefit of a sustained heating effect during the application of a cosmetic composition without being faced with the drawbacks of known methods and devices.

SUMMARY OF THE INVENTION

One aspect of the invention relates to a treatment method for keratinous fibres enabling the use of heat that is compatible with a wide range of cosmetic compositions. The invention further relates, in one of its aspects, to a cosmetic and non-therapeutic method of treating at least one area of the human body.

The composition can be, for example, applied on the skin or the hair just before bringing the applicator into contact therewith. In some cases, the composition can be applied more than an hour or even a day before other aspects of the invention are carried out, depending on the treatment to be carried out.

One example of the invention can be used to treat an area of the human body with the application of heat by means of a cosmetic composition, which can be of any type, given that it is only heated at the time of use in this example. When the composition is taken up from a container, the risk of denaturation, under the effect of the heat, of the unused composition remaining in the container can thus be avoided. In other words, only the portion that is to be used need be heated at any given time.

In one example, the applicator can be used as a massaging implement.

The duration of uninterrupted contact of the composition with the skin and the hair is, for example, between 0.5 seconds and 30 min. The duration can be shorter or longer depending on the treatment carried out.

The addition of heat can boost the action of the composition, for example by preparing the skin for its action, by dilating the pores, by creating hyperaemia, by stimulating the circulation and/or promoting the penetration of the active agents. Further, the applicator can impart a relaxing effect.

The applicator can be used to impart a massaging action with reduced risk of dispensing an excess of composition onto the treated area, given that the applicator can be brought into contact with the treated area without necessarily dispensing composition onto the treated area at the same time.

The temperature to which the applicator is heated can be, for example, in the range of greater than or equal to 50° C. and less than or equal to 80° C.

The applicator can include, in at least one cavity, a compound, in particular a compound capable of changing state when heated. The applicator can be heated to a temperature sufficiently high to produce this change of state. For example, the compound can be a solid which liquefies by the addition of heat. In one example, the compound is a wax. The applicator can recover the latent heat of solidification when the compound cools.

In one example, the applicator can include at least 0.2 cm³ of the compound.

The area to be treated can be the skin of the face or other parts of the body, including the mucous membranes or the hair.

In one embodiment of the invention, the method includes application on the area to be treated of a substrate carrying the composition, the applicator being brought into contact with the substrate thus applied.

In one example, the substrate can include a woven, a non-woven or a foam material.

The cosmetic composition can be taken up from a container to be applied on the area to be treated. The composition can be taken up by means of the applicator or by other means, for example using a finger, a spatula or a dispensing device such as a pump. Further, the container can include a dispensing nozzle.

The first treatment of the same area or of different areas can be effected with an applicator brought to a temperature greater than or equal to 30° C., and a second treatment of the area or areas can be effected with an applicator brought to a temperature below or equal to 15° C., or conversely. In one example, the same applicator is be used for both applications. Different applicators can also be used.

The cosmetic composition can include at least one compound which changes state at the temperature to which the applicator is heated and the heat contributed by the applicator to the cosmetic composition can be sufficient to produce the change of state of at least a part of this compound. The composition can be applied on a wrinkle for example and the applicator can cause the compound to melt instantaneously inside the wrinkle when brought into contact therewith. The compound can be particulate. Further, the compound can include, for example, particles incorporating at least one polymer having a melting point below or equal to the temperature to which an application surface of the applicator is brought, for example greater than or equal to 30° C. Some examples of the compound are solids at room temperature (i.e., ambient temperature, roughly 20-25° C.). The applicator can also be used, as the case may be, at ambient temperature should the user so wish. The composition can be held in a container that is closed when the applicator is in use.

One example of the invention provides an assembly including a non-rotatable applicator. The applicator can be configured to detachably connect to a container or substrate holding a composition. The applicator typically includes an application surface configured to treat an area of skin, and at least one material with thermal properties such that, when the at least one material is heated to a temperature above 30° C. and which temperature does not cause thermal damage to the skin when the application surface is contacted with the skin for 15 seconds, the application surface maintains, after this application, a temperature above or equal to 30° C.

Another example of the invention provides an applicator including a non-rotary application surface including a material with a thermal conductivity greater than or equal to 1 $Wm^{-1}K^{-1}$. The applicator further includes a grasping surface including a material with a thermal conductivity less than or equal to 1 $Wm-1K-1$, and a cavity inside the applicator containing at least 0.2 ml of a compound which changes state at a temperature between 30° C. and 80° C.

Another example of the invention provides a cosmetic non-therapeutic method of treating at least one area of the human body. This method includes providing an assembly including an applicator. The applicator includes at least one material with thermal properties such that, when the at least one material is heated to a temperature above 30° C. and which temperature does not cause thermal damage to the skin when the application surface is contacted with the skin for 15 seconds, the application surface maintains, after this application, a temperature above or equal to 30° C. The method further includes heating the applicator to a temperature above or equal to 30° C., then loading the applicator thus heated with a cosmetic composition at a temperature closer to the ambient temperature than the temperature of the applicator and having a difference of at least 5° C. relative the temperature of the applicator. The method also includes one of the following: i) applying the composition using the applicator, or ii) before or after heating, applying on the area to be treated at least one cosmetic composition, and after heating, bringing the applicator thus heated into contact with the area to be treated.

Another example of the invention provides a cosmetic non-therapeutic method of treating at least one area of the human body. This method includes providing an applicator including a non-rotary application surface including a material with a thermal conductivity greater than or equal to 1 $Wm^{-1}K^{-1}$. The applicator further includes a grasping surface including a material with a thermal conductivity less than or equal to 1 $Wm^{-1}K^{-1}$. The applicator further includes a cavity inside the applicator containing at least 0.2 ml of a compound which changes state at a temperature between 30° C. and 80° C. The method further includes heating the applicator to a temperature above or equal to 30° C., then loading the applicator thus heated with a cosmetic composition at a temperature closer to ambient temperature than a temperature of the applicator and having a difference of at least 5° C. relative to the temperature of the applicator. The method also includes one of the following: i) applying the composition using the applicator, or ii) before or after heating, applying on the area to be treated at least one cosmetic composition, and after heating, bringing the applicator thus heated into contact with the area to be treated.

In one example of the invention, the application surface cannot be rotary. That means that the application surface is not defined by an element assembled in rotation around an axis of rotation, such as for example a rotary ball or a rotary roller. By using a non-rotary application surface, one can apply a great surface having the same relatively high temperature to the area of the skin to be treated, which is not the case when a rotary application element is used.

The applicator can be non-metallic. The compound can be a liquid.

The device can include at least 0.2 $cm^3$ of the compound, preferably between 1 and 80 $cm^3$ of the compound, in particular between 5 $cm^3$ and 70 $cm^3$.

The applicator can include a relatively dense material, for example having a density greater than or equal to 1.5 $g/cm^3$, defining at least partially an application surface intended to come into contact with the area to be treated. This material can be glass or stone, for example.

The applicator can include a material defining at least partially the application surface and having a thermal conductivity greater than or equal to 1 $Wm^{-1}K^{-1}$, preferably 40 $Wm^{-1}K^{-1}$ and/or a material of specific heat capacity greater than or equal to 500 $J\,kg^{-1}K^{-1}$, preferably 1,000 $J\,kg^{-1}K^{-1}$, even more preferably 2,000 $J\,kg^{-1}K^{-1}$. This material can be in contact with the compound contained in the cavity, as the case may be. The applicator can include a material having a specific heat greater than or equal to 500 $J\,kg^{-1}K^{-1}$. This material can be glass or stone, for example.

A high thermal conductivity is conducive to the transfer of heat between the applicator and the area to be treated and facilitates rapid renewal of the heating effect as long as the heat stored by the applicator permits.

The thermal capacity is for example such that at an ambient temperature of 20° C. the application surface retains a temperature above or equal to 30° C. for at least 10 minutes when initially brought to 50° C. (uniform temperature).

The applicator can be such that when heated (in a uniform manner) to 50° C. and applied on the skin, it retains in particular at the application surface for at least 30 seconds, preferably 1 minute, even more preferably 15 minutes or 30 minutes, a temperature above or equal to 30° C.

The application surface can be defined at least partially by a material having a thermal inertia greater than or equal to 1,000 $Jm^{-2}K^{-1}s^{-1/2}$, preferably greater than or equal to 5,000, even more preferably 10,000 $Jm^{-2}K^{-1}s^{-1/2}$.

Thermal inertia characterizes the ability of the application surface to retain its temperature when periodically exposed to contact with the skin.

Thermal inertia is defined by the formula $(K.\rho.C)^{1/2}$, where k is the thermal conductivity, $\rho$ the volume density, and C the specific heat capacity.

The applicator can have a mass greater than or equal to 15 g. A high mass can make it possible to increase the thermal capacity.

The applicator can include a grasping surface defined at least partially by a material having a thermal conductivity less than or equal to 1 $Wm^{-1}K^{-1}$, preferably 0.5, or 0.1 $Wm^{-1}K^{-1}$. This material can include a plastic, for example thermoplastic, or wood. This material can have a cellular structure, for example.

The composition and the applicator can be contained initially in the same packaging.

The applicator can also include materials that are non-metallic but dense, for example having a density greater than or equal to 1.1 $g/cm^3$, preferably 1.5 $g/cm^3$, for example sand, glass or kimberlite.

The applicator can include at least one part that is molded, for example by injection or blow molding, or that is machined.

The aforementioned cavity can be made by molding and/or by machining. The applicator can include more than one cavity containing the compound capable of changing state.

The applicator can include a relatively dense material and a plastic, a glass and a plastic, for example.

The application surface can be soft and polished or as a variant can include asperities or projections such as raised points.

The application surface can be defined by a material that is hard or otherwise. As the case may be, the application surface can be defined at least partially by a wall at least partially covered by an elastomer membrane, a foam, a flock material, a plastic film, a sponge, a felt, a woven material or a non-woven material. The wall thus covered is for example formed at least partially by a metallic material.

The applicator can be designed to be detachably mounted on the container. The applicator can be designed to be detachably fixed on a closure element of the container. The applicator can optionally serve as closure element for a container holding the composition.

The applicator can also be designed to be detachably fixed on a dispensing device enabling the composition to be taken up.

The container can also include an extension having a recess capable of receiving the applicator.

As the case may be, the applicator and the container can be contained in a common packaging device, for example a box, a carton pack, a blister pack, a film pack or a sachet.

The applicator can include a rotary applicator element designed to come into contact with the area to be treated, or a plurality of rotary applicator elements, which can fold and move the skin during their passage, for example.

The applicator can be at least partially magnetic.

The applicator can include a flexible lip, for example arranged in the manner of a suction cup.

The applicator can include a passage enabling the composition to be dispensed when the applicator is mounted on the container. The composition can come into contact with this passage or the latter can receive a dispensing nozzle in which the composition circulates.

The applicator need not include compounds that react together by an exothermic reaction.

The applicator can include a detachable vibrator and/or at least one detachable electrode connected to a power source, for example two electrodes between which a potential difference is established.

The container can have an internal space containing the composition, of variable volume.

The applicator can have an application surface defined at least partially by a detachable part. The latter is, for example, at least partially composed of an absorbent material and includes for example a cellular material and/or fibres, or bristles, and can, for example, be detached from the applicator to be washed. The detachable part can, for example, improve spreading of the composition on the area treated by means of the applicator.

The applicator can have a reduced thickness ($e_{min}$) between the aforementioned cavity and the application surface, less than or equal to 50 mm, preferably less than or equal to 10 mm, even more preferably less than or equal to 1 mm, for example, between 0.1 mm and 1 mm, for example between 0.2 mm and 0.8 mm, so as to promote heat transfer between the application surface and the liquid contained in the cavity.

The applicator can include at least one temperature indicator, for example, a thermochromic indicator. The temperature indicator can change color to warn the user that the application surface is at a temperature above or below a pre-set threshold, for example.

The applicator can include a take-up element for the composition held in the container. This take-up element includes, for example, a foam, an agglomerate material, a felt, a woven material, a non-woven material, a flock material, or bristles. The take-up element can be located at an end of the applicator opposite the application surface.

The applicator can include a first part assembled with at least one second part, for example, by force fit, snap attachment, screwing, welding, gluing, over-molding or crimping.

The first part can form the application surface and can include a relatively dense material, for example. The second part can form the grasping surface and can include a less dense material. The first or the second part can include an opening for filling of the cavity containing a liquid or other compound capable of storing heat.

The container can include a first compartment containing the composition and a second compartment to receive the applicator and a closure element enabling the first and second compartments to be closed at the same time. The container can also include a central recess to at least partially receive the applicator.

The packaging and applicator device can include a first applicator intended to be cooled and a second applicator intended to be heated. The first can contain a liquid and include a metallic material and the second can be devoid of metal.

The cavity can be defined by a non-constant thickness wall.

The applicator can be configured so that the cavity is not accessible from outside. In other words, the cavity can be hermetically sealed. Thus, by the expression "not accessible from outside", one understands that no passage which can open to reach inside the cavity is envisaged in the applicator, once of course that the cavity was filled during manufacture of the applicator.

As should be apparent, the invention can provide a number of advantageous features and benefits. It is to be understood that, in practicing the invention, an embodiment can be constructed to include one or more features or benefits of embodiments, disclosed herein, but not others. Accordingly, it is to be understood that the preferred embodiments discussed herein are provided as examples and are not to be construed as limiting, particularly since embodiments can be formed to practice the invention that do not include each of the features of the disclosed examples.

BRIEF DESCRIPTION OF THE DRAWINGS

A better understanding of the invention will be gained from reading the following description in conjunction with the accompanying figures. The figures are offered purely as a guide and for purposes of example and in no way limit the invention.

FIG. 1 illustrates an elevation of a device made according to one example of the invention;

FIG. 2 is a schematic longitudinal cross-section of the device shown in FIG. 1;

FIG. 3 separately illustrates an alternative example of an applicator according to the invention;

FIG. 4 is a view similar to FIG. 1 of an alternative example of a device according to the invention;

FIG. 5 separately illustrates an elevation of the applicator shown in FIG. 4;

FIG. 6 is a perspective view of an alternative example of a device according to the invention;

FIG. 7 is a longitudinal cross-section of the device shown in FIG. 6;

FIGS. 8 to 12 are schematic and partial longitudinal cross-sections of devices according to alternative examples of the invention;

FIGS. 13 and 14 are schematic perspective illustrations of example kits for putting one aspect of the invention into effect;

FIG. 15 illustrates a use of the kit in FIG. 14;

FIG. 16 is a schematic illustration of another example of a kit for putting one aspect of the invention into effect;

FIG. 17 illustrates the applicator shown in FIG. 16 during use;

FIGS. 18 to 24 and 26 to 28 are schematic longitudinal cross-sections of alternative examples of the applicator;

FIGS. 29 and 39 are schematic perspective illustrations of other examples of the applicator;

FIG. 30 is a partial longitudinal cross-section of the applicator shown in FIG. 29;

FIGS. 31 to 34 and 38 are elevation views of alternative examples of the applicator;

FIGS. 35 to 37 and 40 to 53 are schematic and partial longitudinal cross-sections of alternative examples of the applicator;

FIG. 57 is a schematic illustration of a safety capsule for the applicator.

DETAILED DESCRIPTION OF THE PREFERRED EMBODIMENTS

Figure 42:
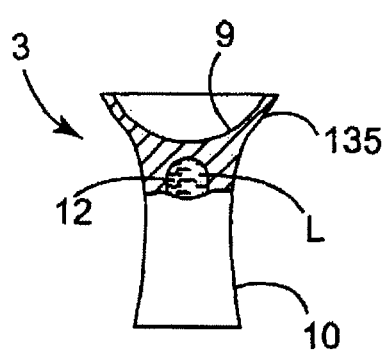

Referring now to the drawings, wherein like reference numerals are used to designate identical or corresponding parts throughout the several views.

The packaging and applicator device 1 illustrated in FIGS. 1 and 2 includes a container 2 holding a cosmetic composition P, which is typically meant to be applied on the human body and an applicator 3, of axis X. The applicator 3 is typically held by a user to apply the composition P. The composition P is often configured to impart at least one beneficial action such as anti-wrinkle, contouring, moisturizing, coloring, anti-acne, anti-seborrheic, bleaching, stimulating, regenerating or soothing actions, and/or to conceal skin blemishes. The cosmetic composition P can be, for example a compound such as is defined in Directive 93/35/EEC of 14 Jun. 1993, amending Directive 76/768/EEC.

One type of composition P, for example, does not withstand prolonged storage in the container 2 at a temperature above or equal to 55° C. However, other compositions with other shelf-lives are possible. The composition P can contain at least one compound that changes state at a temperature between 30° C. and the temperature to which the applicator is brought. By "changes state," it is meant that the compound changes from/to a gas, liquid, or solid to/from another state such as gas, liquid, or solid. It can include a dispersion of particles, in a wax, for example. In the example shown in FIG. 2, the container 2 takes the form of a pot including a body 4 provided at the top with a threaded neck 5 and a cover 6 capable of being detachably fixed on the neck 5, for example by screwing. The cover 6 and the neck 5 can include sealing means enabling the container 2 to be closed in a leaktight manner. One example of such sealing means includes an o'ring. Another example of sealing means includes a compliant material comprising portions of one or both of the cover 6 and the neck 5.

In the example shown in FIG. 2, the cover 6 includes an upper wall 8 defining a recess 7 open at the top, in which the applicator 3 can engage when not in use. The applicator 3 is, for example, held by friction in the recess 7. The applicator 3 has an application surface 9 configured to come into contact with the area to be treated, for example the skin, and a grasping surface 10 capable of being grasped by the user to manipulate the applicator 3. The application surface 9 is typically located on the side opposite the container 2 when the applicator 3 is received in the recess 7.

The grasping surface 10 is typically a lateral surface extending from a lower face of the applicator, for example over more than a third of the total height of the applicator, for example over substantially half of its total height.

In the illustrated example, the applicator 3 includes an internal cavity 12 which can contain a compound L, intended to store heat, for example a wax, an oil or water. In the case of a wax for example, the wax typically has a melting point between 30° C. and 80° C., for example. The quantity of compound L ranges for example from 0.5 to 10 cm$^3$, depending on the amount of heat energy intended to be stored. In one variant, the cavity 12 is filled with a powder, for example, sand. The compound L will typically be able to withstand heating, even repeated heating and cooling to and from temperatures in the range of 30° C. and 80° C. without deterioration affecting its chemical and thermal properties.

In the example considered, the internal cavity 12 is formed between a first part 16 which defines the application surface 9 and a second part 14, which is typically assembled with the first part. The first part 16 is typically made of glass or a ceramic compatible with placement in a microwave oven. As such, the first part 16 is "microwave safe." In other words, heating the first part 16 in a microwave will not result in sparking or destruction of the first part 16. The second part 14 is typically made of plastic and includes, in the example shown in FIG. 2, a sealing lip 18 of axis X which covers the first part 16 so as to produce a leak-tight assembly. The first part 16 typically includes an upper wall 29 of which the thickness, measured on the axis X, can for example decrease towards the axis X so as to promote heat transfer between the cavity 12 and the application surface 9 in the central region of the applicator 3. In other examples of the invention, the wall thickness does not vary, or varies in a different manner.

Assembly of the first and second parts, in the example in FIG. 2, can be accomplished in a variety of ways, for example by screwing, force fit, gluing, snap attachment, welding, overmolding or crimping.

In the example illustrated in FIG. 3, the applicator 3 does not include the cavity 12 filled with the liquid L. In this example, the first part 16 is solid and made of a material having sufficient thermal capacity and thermal conductivity to obtain the desired result. This material can include, for example, glass, stone, or a loaded plastic.

The second part 14 can be effective in thermally insulating the grasping surface 10 and can be made of a plastic having a thermal conductivity less than or equal to 1 $Wm^{-1}K^{-1}$, or of wood, for example.

In a variant not illustrated, the applicator can also be made in one piece in a single material.

In the example shown in FIG. 37, the first part 16 is for example formed from a plate or plate-shaped component. The second part 14 is configured to enable the first part 16 to be fixed by snap attachment. The second part 14 can include a groove 280 adapted to receive a seal 281 bearing on the inner surface of the first part 16. The first part 16 is typically fixed on the second part 14 after filling the latter with the compound L.

The applicator 3 can be made with a shape adapted to the area of the body to be treated. The applicators 3 depicted in FIGS. 1 to 3 are relatively wide, for example wider than tall, and are intended for example to treat an area other than the face.

FIG. 4 illustrates a packaging and applicator device 1 having a narrower applicator 3, better adapted to the face. It can be seen in FIG. 5 that the height of this applicator 3 is greater than its width for example.

FIGS. 6 and 7 depict a device according to an alternative embodiment of the invention in which the container 2 has a central recess 30 in which the applicator 3 can at least partially engage. The recess 30 can extend fully through the first part 14 as illustrated in FIG. 7.

The applicator 3 is typically designed to rest on a bearing surface 35 against the top of the cover of the container 2, the applicator 3 being generally mushroom-shaped for example. The bearing surface 35 can thus have an annular shape. The applicator 3 of FIG. 7 can, as illustrated, be formed with the cavity 12 and the latter extends for example at least partially into the recess 30 when the applicator 3 is in place on the container 2. The bearing surface 35 can be defined by the first part 16.

To use the applicators 3 as exemplified in FIGS. 1 to 5, the user can heat them by placing them in a microwave oven. The container 2 holding the cosmetic composition P can be held at a temperature below that of the applicator 3, for example being retained at the ambient temperature outside the microwave oven. The user can then procure a portion of the composition P from the container 2, for example with the finger, and apply it on the area to be treated or on the applicator 3. The applicator 3 is typically then brought into contact with the area to be treated.

The applicator 3 can be used by being moved in contact with the skin, for example by circular or linear movements, to impart a massaging action and/or to spread the composition P. The user can also proceed by applying successive pressure at different points without substantial movement of the applicator on the skin to effect a thermo-puncture treatment, for example. The applicator 3 can also touch the skin. It is also possible to impart an effect equivalent to hot ironing of the skin or of a substrate applied to the skin.

As discussed above, either the user's finger or the applicator 3 can be used to take up the composition P from the container 2. FIG. 8 illustrates the container 2 in the form of a tube having a dispensing nozzle closed off by a closure cap 32.

In the example shown in FIG. 8, the applicator 3 is configured to be fixed on the closure cap 32 by a recess 33 formed in the body 34 of the applicator. Retention of the applicator 3 on the cap 32 can be provided, for example, by friction or other means such as by snap attachment or screwing. The body 34 can be made with the cavity 12 accommodating the compound L, as illustrated, or can be solid.

To use the applicator 3, the user can separate it from the container 2 and place it in the microwave oven. The user can then dispense the composition held in the container 2 onto the applicator 3 or onto the area to be treated. The user can use the body 34 as a grasping element without replacing the applicator 3 thereon, or as a variant can use the applicator 3 after reattaching it to the container 2, the latter then defining the grasping surface.

FIG. 9 depicts an alternative embodiment in which the container 2 is a bottle provided with a neck, and the body 34 serves as a closure cap by being screwed onto the neck. The composition P is held within the bottle, and the application surface 9 may be configured to be inserted into the bottle to procure a portion of the composition P.

The composition P can be held in a container 2 such as that illustrated in FIG. 10, which includes a first compartment 36 to receive the composition P and a second compartment 37 to receive the applicator 3.

In the illustrated example, these two compartments 36 and 37 are closed off by a common cover 38, which includes, for example, a sealing skirt 39 so as to close the first compartment 36 in a leak-tight manner.

In the example illustrated in FIG. 10, the cover 38 is designed to screw on, but in variants not illustrated, the cover 38 is attached by other means, being for example inserted or retained by a hinge on the container 2.

The second compartment 37 can contain several applicators 3 having different shapes and/or intended to be used differently, for example by being cooled in at least one instance and heated in at least one other instance.

The composition P can, as illustrated in FIG. 11, be held in a container 2 incorporating an extension 40 designed to accommodate the applicator 3. The extension 40 extends, for example, laterally and can include a recess 41 of a shape adapted to receive the applicator 3.

As shown in FIG. 12, the composition P to be applied can be provided to the user together with at least two applicators 3, one being configured to be cooled and the other to be heated. These two applicators 3 can be provided to the user in the form of a kit with the container 2 holding the composition P. The kit typically includes a holder 45 configured to accommodate the container 2 and the applicators 3 when not in use.

The holder 45 can include, for example, a recess 46 configured to receive the container 2 holding the composition P and two recesses 47 and 48, each receiving an applicator 3. In a variant not illustrated, the container 2 is integrally formed in one piece with the holder 45. The container 2 can also be provided to the user with at least one applicator 3 in packaging such as a box 50 for example, as illustrated in FIG. 13.

The composition P can take the form of a powder, cream, paste, gel or liquid, or can impregnate and/or coat a substrate such as for example a woven material, a non-woven material, a foam, or a felt.

The substrate 52, in the form of a mask or a patch, for example, can be applied onto the skin, and the heated applicator 3 is then brought into contact therewith, as illustrated in FIG. 15.

As illustrated in FIG. 14, the substrate 52 can be contained in an individual pack 53 and be proposed to the user in the form of a kit in conjunction with at least one applicator 3. The set is typically contained in a pack 54, as illustrated in FIG. 14. In a variant not illustrated, a plurality of substrates can also be provided to the user in a common package rather than in individual packaging.

The substrate impregnated with composition can optionally be substantially anhydrous and can be wettable by a solvent such as water, for example, at the time of use.

FIG. 16 depicts another example of a kit for putting the invention into effect. In the illustrated example, the applicator 3 includes a recess 60 configured to receive a substrate 62 containing the composition to be applied, or the composition itself shaped so as to fit into the recess 60. The composition P in this case can be block shaped so as to accommodate a similar shaped recess 60. The substrate 62 or the block of composition can be contained in an individual pack 64, for example. In one example of the invention, the quantity of composition contained in the substrate 62 or constituting the block can correspond to a single use. During use, the user removes the substrate 62 or the block of composition from the pack 64 and inserts it into the recess 60 of the applicator. The depth of the recess 60 is for example smaller than that of substrate 62 so that the user can apply the composition onto the area to be treated. The recess 60 is typically formed of a glass, ceramic or stone part of the applicator 3, so as to promote heat exchange between the substrate 62 or the block of composition and the applicator 3. The substrate 62 or block of composition can be placed on the heated applicator 3. After application, the substrate 62 can be withdrawn from the recess 60.

The applicator 3 can also be made in a variety of other ways. The cavity 12, which contains the compound L, can in particular be closed in different ways. FIG. 18 depicts an embodiment in which the first part 16 and second part 14 cooperate by screwing and the second part 14 includes a sealing lip 70 which bears on a radially inner surface of the first part thereby closing the cavity 12 in a leak-tight manner. The second part 14 can include a threaded skirt 71 which partially covers the first part 16 and which defines the grasping surface 10.

In the alternative embodiment illustrated in FIG. 19, the first part 16 and second part 14 are assembled with the interposition of a seal 72. The second part 14 is typically threaded on the side exposed the first part 16, which can be screwed onto the second part 14.

The applicator 3 can also include a body 76 defining the grasping surface 10 and the application surface 9, as illustrated in FIG. 20. The body can be recessed to define the cavity 12 filled with the compound L.

The cavity 12 can be closed with a plug 78, which can be fixed on the body 76 by various means, such as by snap attachment. The plug 78 can include an annular sealing lip 79 bearing on a surface of the body 76 delineating the cavity 12.

FIG. 21 depicts an alternative embodiment similar to that shown in FIG. 18. However, in the example illustrated in FIG. 21, the second part 14 includes a skirt 71 which extends to the wider portion of the first part. In addition, the thickness of the first part 16 between the cavity 12 and the application surface is smaller.

The applicator 3 shown in FIG. 22 differs from that depicted in FIG. 20 in that the cavity 12 is closed by a bottom 80 which is for example welded to the body 76 around the opening used to fill the cavity 12. The bottom 80 is for example a sheet of a material impermeable to the compound L, which can be transparent so that a user may view the compound L inside the cavity 12.

The applicator 3 can be made with a wide variety of external shapes, for example, an elongated shape with a widened head, as illustrated in FIG. 23.

In some examples, the cavity 12 can extends over the majority of the height of the applicator. In the example in FIG. 23, the cavity 12 extends over more than half of the length of the applicator 3, in this instance practically over the whole of its length.

In the embodiment depicted in FIG. 24, the applicator 3 has a rounded head. This figure illustrates the possibility for the applicator to include an application surface 9 defined by a coating 300 covering a wall 301 delineating the cavity 12. The coating 300 is for example an elastomer membrane, a woven or a non-woven material.

Figure 25:
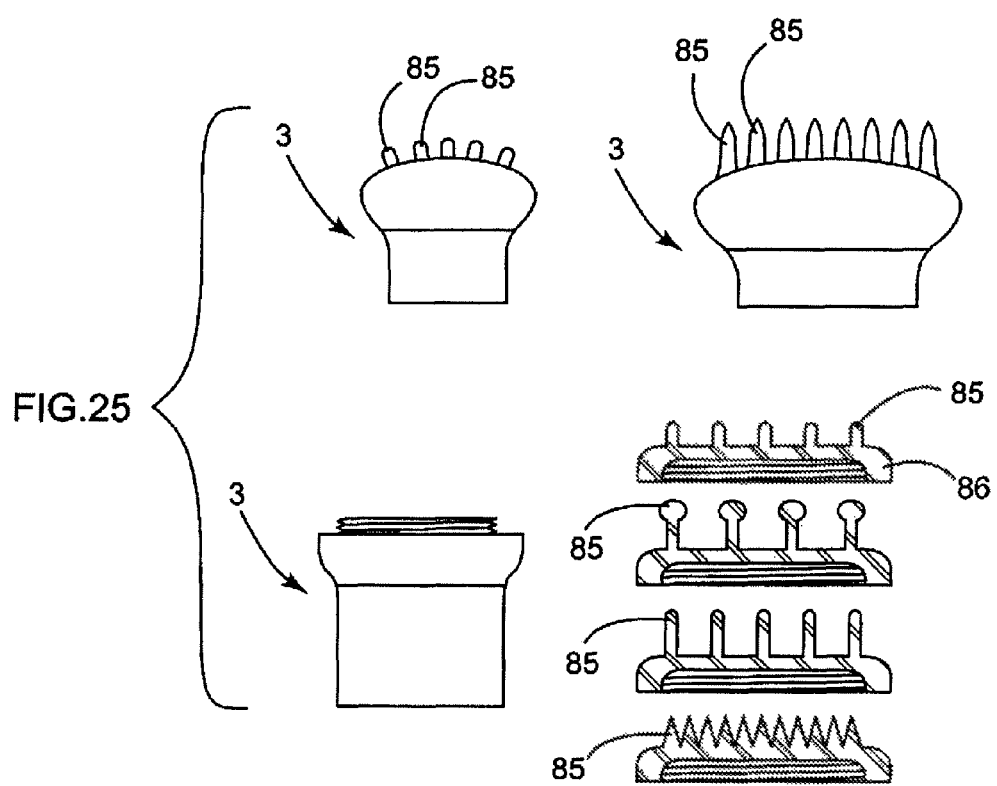
FIG. 25 illustrates alternative examples of the applicator.

The application surface 9 of the applicator 3 can include projections, for example raised points 85, as illustrated in FIG. 25. The projections 85 can be made of an elastomer material, for example. The projections 85 can be formed on a detachable part 86, which makes it possible to choose the projections 85 depending on the treatment to be effected. Attachment of the component 86 can be accomplished by screwing, for example.

The applicator 3 can include an application surface 9 having a flat portion as illustrated in FIG. 26, which can extend obliquely relative to the longitudinal axis X of the applicator 3, for example.

It can also be seen in FIG. 26 that the cavity 12 can include an opening enabling it to be filled with the compound L, and this opening can be closed off by a plug 88 formed for example by a drop of glue.

FIG. 27 depicts an applicator 3 which includes a first part 16 defining the cavity 12 filled with the compound L and a second part 14 having the form of an elongate handle which may not be traversed by the cavity 12, as illustrated.

The application surface can also be defined by a head 90 which is connected to the rest of the applicator by a narrow portion 91 as illustrated in FIG. 28. The narrow portion 91 can be flexible and can typically bend during use. The first part 16 is for example snapped into the second part 14, the cavity 12 being formed inside the first part 16 and closed off at one end by the second part 14.

The application surface 9 of the applicator 3 can be defined at least partially by a fitted part 95 made of a resiliently deformable material, for example, a foam, as depicted in FIGS. 29 and 30.

The fitted part 95 can have an annular shape and can be mounted on an extension 96 of the applicator body 98. The top 99 of the extension 96 can also serve as the application surface. The component 95 can be cleaned after it has been used.

FIG. 29 illustrates the provision for the applicator 3 to include a temperature indicator 305, which can change color and indicate to the user that the application surface 9 is at an acceptable temperature for the treatment to be effected.

The application surface 9 can include, as can be seen in FIG. 31, at least one depression 100 allowing an accumulation of product, or a slot 101 as illustrated in FIG. 32. The application surface 9 can be defined at one end by a point, as illustrated in FIG. 33, or by a beveled end face as illustrated in FIG. 34.

FIG. 33 illustrates an example in which the application surface 9 includes a flock covering 310.

The application surface 9 can also include, as illustrated in FIG. 35, a mass 103 of a heat conducting material, fixed in a recess 104 of a first part 105 of the applicator 3. This first part can define the cavity 12 including the compound L, and can be supported by a grasping part 106 made of a poorer heat-conducting material than that of the first part 105. The mass 103 is, for example a ceramic, a glass, or a dense stone.

FIG. 36 illustrates an example in which the application surface 9 is formed by a part 110 which is in direct contact with the compound L contained in the cavity 12. The part 110 is for example made of glass, and the cavity 12 is formed inside a body 111 made of insulating plastic. A plug 112 can be screwed onto the body 111 to close the bottom of the cavity 12.

The applicator 3 can include two application surfaces 9 having different shapes, as illustrated in FIG. 38. For example, an application surface having a rounded shape and an application surface having a beveled shape can efficiently be used to apply the compound P. An insulating ring 118 can be provided in a median region of the applicator 3 to define the grasping surface 10. The differently shaped application surfaces 9 are, for example, located at opposite ends of the applicator 3.

The applicator 3 can alternatively include application surfaces 9 having different shapes or otherwise, located at the same side, as illustrated in FIG. 39. The applicator 3 can, for example, be U-shaped, the ends of the U defining the application surfaces 9, and the base of the U defining the grasping surface 10.

The applicator 3 can be designed so that, when it is resting on a flat surface S, as illustrated in FIG. 40, it allows the compound L contained in the cavity 12 to come into contact with the wall 120 which defines the application surface 9.

As illustrated in FIG. 41, the applicator 3 can be placed on a holder 130 when not in use.

The applicator 3 can be at least partially resiliently deformable, and the application surface 9 can be defined at least partially by a flexible lip 135 making it possible to create a suction cup effect, as illustrated in FIG. 42.

Figure 43:
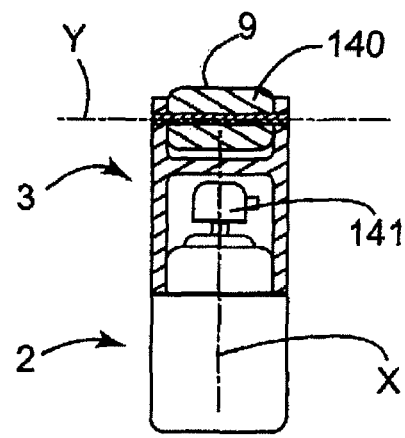

The application surface 9 can also include a mobile member, for example, a roller 140 as illustrated in FIG. 43, turning about an axis of rotation Y which perpendicular to the longitudinal axis X.

FIG. 43 illustrates the provision of the container 2 to be equipped with a dispensing device 141 such as a pump or a valve, making it possible to dispense the composition onto the area to be treated or the application surface 9 before placing it in contact with the skin.

Figure 44:
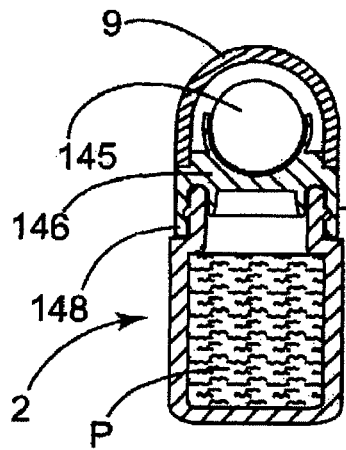

The application surface 9 can also include a rotating member such as a ball 145, as illustrated in FIG. 44. The ball can be carried by a holder 146 which can be detachably mounted on the container 2. Thus, the user can detach the holder 146 in order to heat it, for example, in a microwave oven, without exposing the composition P held in the container to the microwaves. The ball can include the cavity 12 and the compound L. Once heated, the holder 146 can be reattached to the container 2 and the container 2 used as a grasping element. In one example, a skirt 148 on the applicator 3 enables it to be attached on the container 2, which can define the grasping surface 10.

Figure 45:
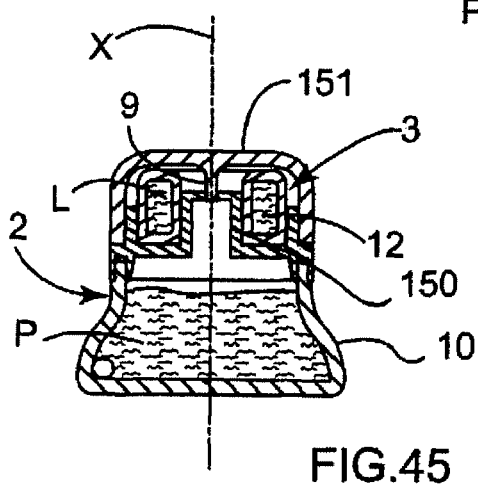

FIG. 45 depicts an alternative embodiment in which the application surface 9 can be defined by an applicator 3 of generally annular shape, which is typically placed around an upstand 150 on the container 2 through which the composition P is dispensed. A closure element 151 can be fitted on the container 2 to close off the upstand 150 when not in use. To use the applicator 3, the user detaches it from the container 2 and places it in a microwave oven. Once heated, the applicator 3 is typically refitted around the upstand 150 and the container 2 can be used as a grasping element to bring the application surface 9 into contact with the area to be treated.

Figure 46:
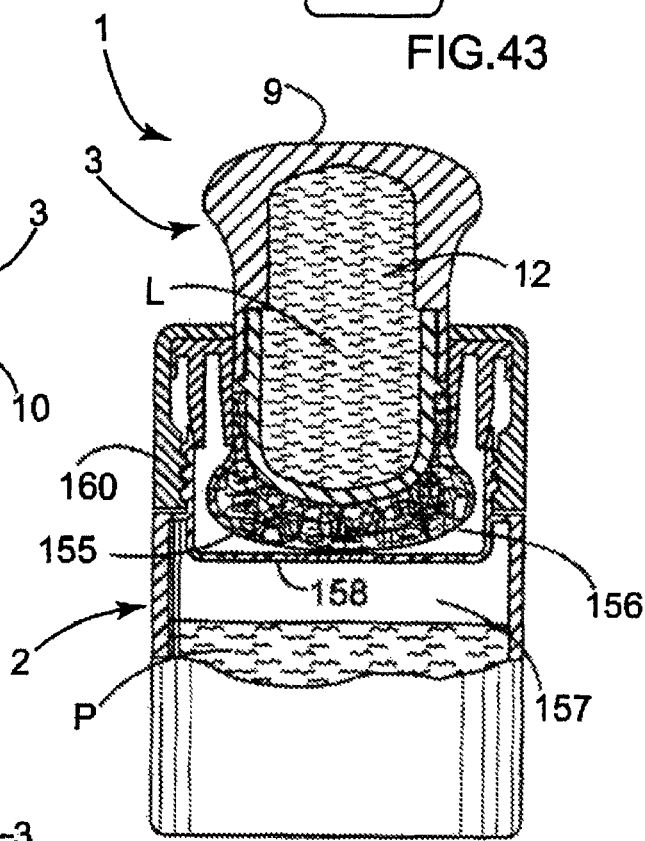

In the example shown in FIG. 46, the applicator 3 includes an application surface 9 intended to apply heat in the area to be treated and an element 155 for taking up the product held in the container 2. This take-up element 155 is, for example, located on the applicator 3 on the side opposite the application surface 9.

The container 2 typically includes a recess 156 to receive the take-up element 155, this recess 156 being separated from a space 157 containing the composition P by a perforated wall 158 which limits the quantity with which the take-up element 155 can be loaded. The latter can be used to apply the composition P on the area to be treated.

The applicator 3 can be integral with a closure element 160 of the container 2. In one example, the closure element is configured to be screwed on the container 2.

To use the device 1 shown in FIG. 46, the user separates the applicator 3 from the container and places the latter in a microwave oven. The user then takes up the composition P from the recess 156, for example after shaking the device 1 with the applicator 3 in place, and can apply the composition contained in and/or on the take-up element 155 by means of the applicator 3. Once the composition has been applied, the user can turn the applicator 3 around and use the application surface 9 to apply heat. The user typically separates the applicator 3 from the container and places the applicator 3 in a microwave oven for heating.

Figure 47:
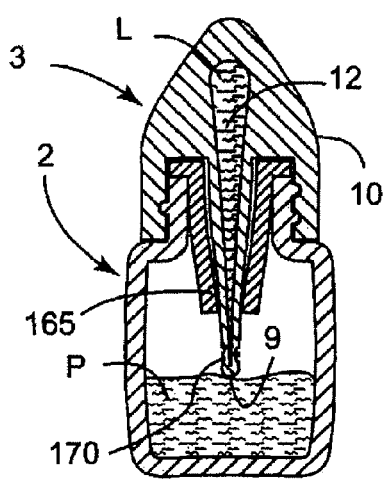

In the example shown in FIG. 47, the application surface 9 is configured to come into contact with the composition inside the container 2. The container 2 can include a wiper element 165, which makes it possible to remove any excess product that may be present on the applicator 3. The applicator 3 can include projections 170 making it possible to increase the quantity of product with which the applicator is loaded and/or making it possible to impart greater flexibility to the applicator as it passes over the area to be treated.

Figure 48:
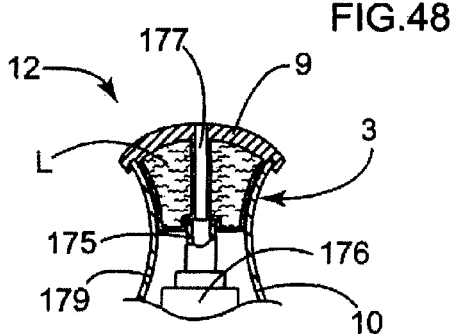

As shown in FIG. 48, the applicator 3 can be configured to be mounted on a dispensing device 175 such as a pump or valve, including a stem 176 which, when depressed and/or tilted, causes the composition P to be dispensed. As further shown in FIG. 48, the applicator 3 can include an internal channel 177 enabling the product delivered by the stem 170 to reach the application surface 9.

In the example shown in FIG. 48, the applicator 3 includes a covering skirt 179 making it possible to conceal all or part of the dispensing device 175 and also defining a grasping surface for the user. The device 1 in FIG. 48 is typically used by first separating the applicator 3 from the dispensing device 175 and then heating the applicator 3 independently of the dispensing device 175. The applicator 3 is then reattached to the dispensing device 175 and, by actuating the applicator 3, the user can cause product to be dispensed through the channel 177. In one example, the user pushes the applicator 3 down to actuate the pump and dispense the product through the channel 177. In another example, the actuator is actuated independently of the applicator 3.

Figure 49:
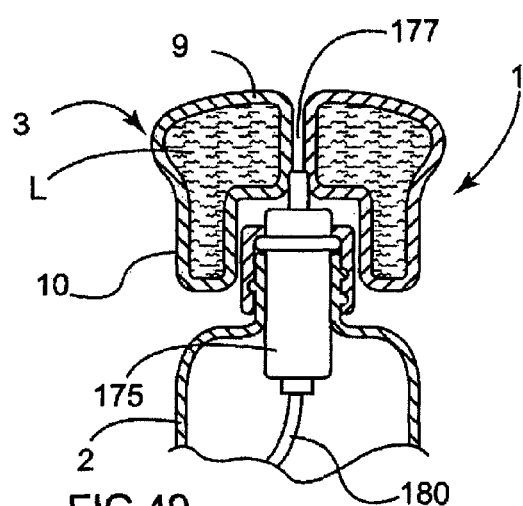

FIG. 49 illustrates a variant in which the dispensing device 175 includes a pump fed by an immersion tube 180.

Figure 50:
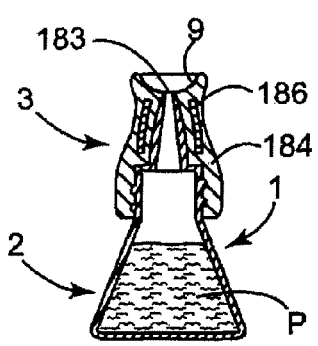

In the example shown in FIG. 50, the applicator 3 can be screwed onto the neck of a container and has for example a convex application surface 9 facing toward the bottom of the container 2. An aperture 183 for delivery of the composition P connects to the surface 9. The body 184 of the applicator can include an insert 186 configured to increase the thermal inertia of the applicator 3.

Figure 51:
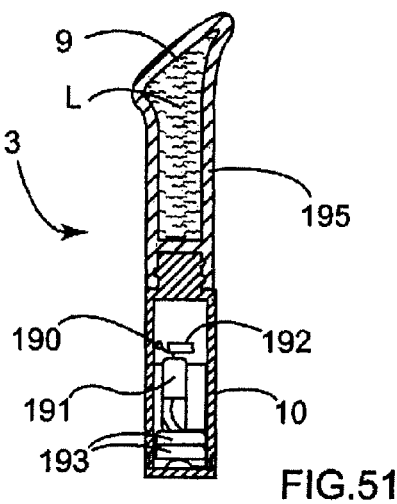

Irrespective of the shape of the applicator 3, it can be equipped with a vibrator 190, as illustrated in FIG. 51.

Such a vibrator 190 includes for example a motor 191 rotationally driving an offset weight 192 so as to produce vibrations. The motor 191 can be powered by one or more cells 193, optionally rechargeable.

The vibrator 190 is typically designed to be detachably mounted on a part 195 of the applicator including the application surface 9, so as to enable the user to use the same vibrator with different application surfaces 9 and to be able to place the applicator in a microwave oven without the vibrator.

Figure 52:
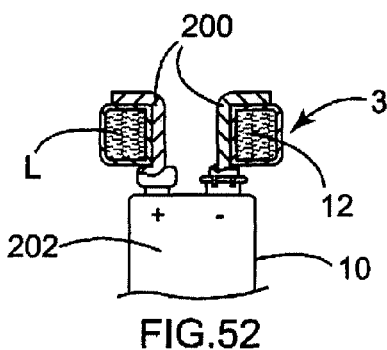

As shown in FIG. 52, the applicator 3 can also include at least one electrode, for example two electrodes 200, to electrically stimulate the treated area during the application. These electrodes are for example electrically connected to a cell 202 which defines the grasping surface 10. In some examples of the invention, it possible to heat the electrodes 200.

To use the applicator 3 shown in FIG. 52, the user can separate the applicator 3 from the cell 202 and the electrodes and place the applicator 3 in the microwave oven. Once the desired temperature is reached, the user can reattach the applicator 3 to the cell 202 and use the latter as a grasping element to bring the electrodes 200 into contact with the area to be treated.

Figures 53, 57:
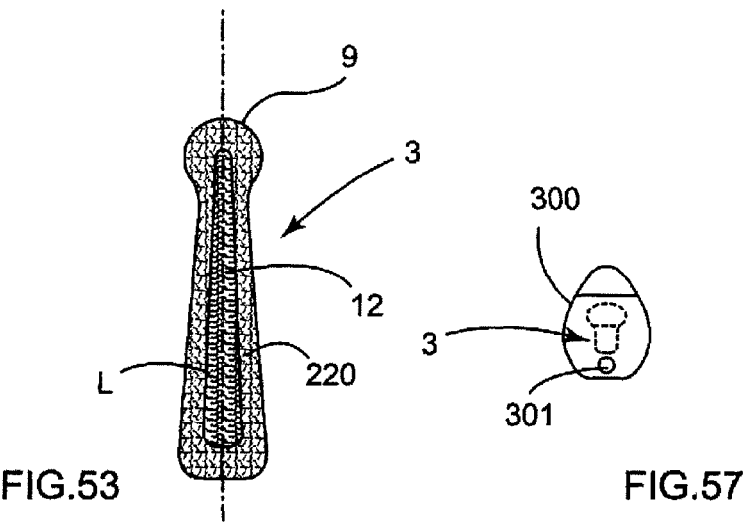

The applicator 3 can also have magnetic properties. By way of example, FIG. 53 illustrates an applicator 3 which includes a body 220 loaded with magnetic particles. In the example illustrated, the body 220 can also define at least partially the cavity 12 containing the compound L. The presence of a magnetic field can increase the thermal capacity of the applicator 3.

Figure 55:
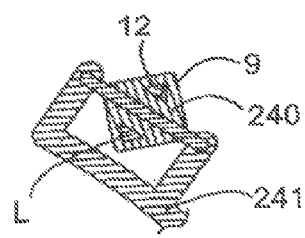
FIG. 55 is a schematic and partial cross-section of one example of the applicator.
Figure 54:
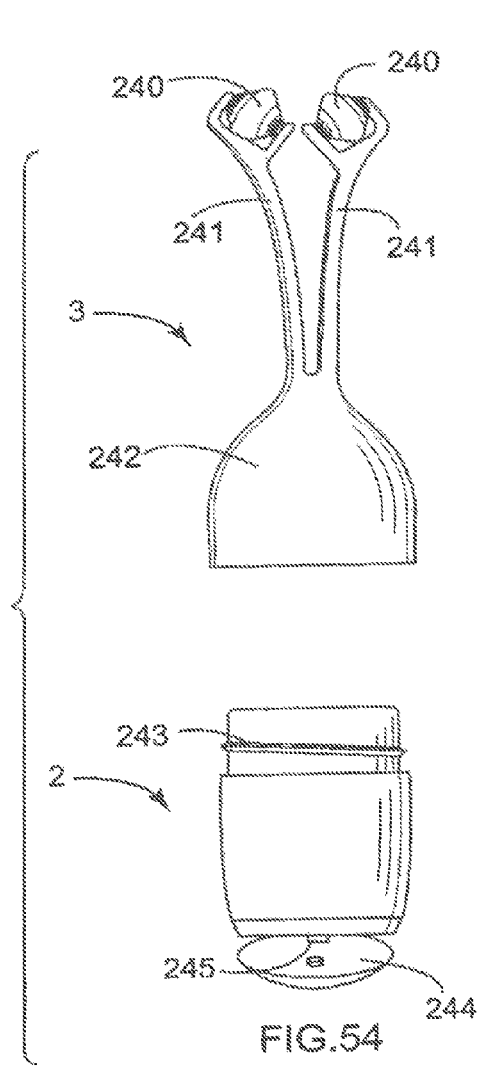
FIG. 54 is perspective view of another example of a packaging and applicator device.

FIGS. 54 and 55 illustrate a packaging and applicator device having an applicator 3 including two rollers 240 mounted on flexible rods 241 connected to a base 242 making it possible to render the applicator 3 integral with the container 2.

As shown in FIG. 54, one example of the container 2 includes at one end a screw thread 243 for attachment of the applicator 3 to the container 2 and at the opposite end a cover 244 serving to close off a dispensing aperture 245. The rollers 240 are designed to provide the desired thermal capacity and can have cavities filled with the compound L.

Figure 56:
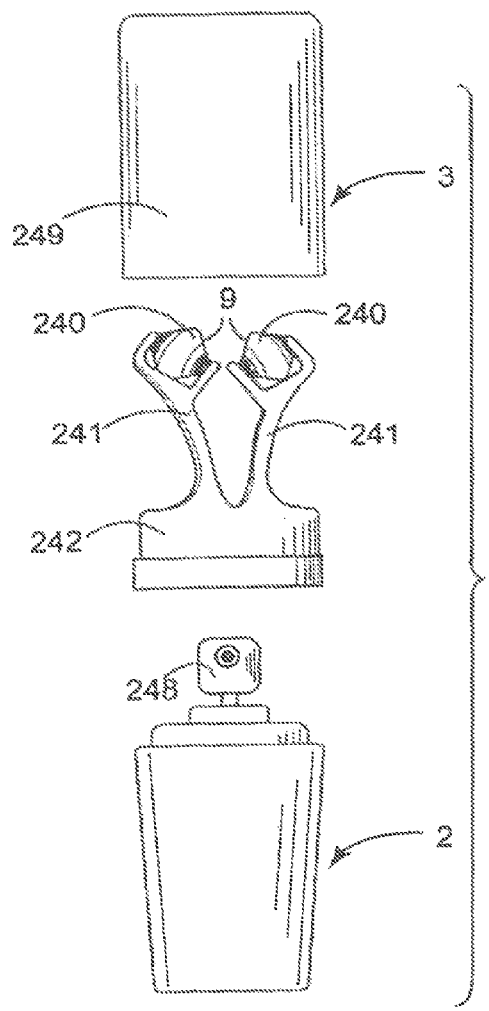
FIG. 56 is a view similar to FIG. 54 of an alternative example.

In the variant illustrated in FIG. 56, the container 2 is equipped with a dispensing device 248 such as a pump or valve. The composition is, for example, held under pressure in the container 2. As further illustrated in FIG. 56, the applicator 3 can include a protective cap 249 to protect the application surface 9 when not in use.

As illustrated in FIG. 57, the applicator 3 can be placed in a safety capsule 300 when it needs to be heated by means of a microwave oven. The safety capsule 300 can include for example a temperature indicator 301.

The invention is not limited to the examples described above. It is possible in particular to combine the particular features of the various embodiments illustrated. It is possible for example to equip any one of the applicators described with a vibrator.

Throughout the description and claims, expressions such as "including one", "having one," "has one", or "comprises one" should be regarded as synonymous with "including at least one", unless otherwise specified.

Obviously, numerous modifications and variations of the present invention are possible in light of the above teachings.

It is therefore to be understood that within the scope of the appended claims, the invention may be practiced otherwise than as specifically described herein.

What is claimed as new and desired to be secured by Letter Patent of the United States is:

1. An assembly including:
a non-rotatable applicator including
an application surface configured to treat an area of skin, and
at least one material with thermal properties such that, when the at least one material is heated to a temperature above 30° C. and which temperature does not cause thermal damage to the skin when the application surface is contacted with the skin for 15 seconds, the application surface maintains, after this application, a temperature above or equal to 30° C.,
wherein the applicator includes at least one closed cavity containing a compound configured to be heated to a temperature above or equal to 30° C. and below or equal to 80° C. without deterioration.

2. The assembly according to claim 1, wherein the applicator is microwave safe.

3. The assembly according to claim 1, further including a cosmetic or dermatological composition, different from the compound.

4. The assembly according to claim 3, wherein the applicator includes a passage enabling the composition to be dispensed while the applicator is mounted on a container.

5. The assembly according to claim 1, wherein the compound changes state when heated to a temperature between 30° C. and 80° C. from a temperature below 30° C.

6. The assembly according to claim 1, wherein the cavity includes at least 0.2 cm³ of the compound.

7. The assembly according to claim 1, wherein the applicator includes between 1 and 80 cm³ of the compound.

8. The assembly according to claim 1, wherein the applicator includes, between the cavity and an application surface to be brought into contact with the area to be treated, a wall with a smallest thickness ($e_{min}$) less than or equal to 50 mm.

9. The assembly according to claim 1, wherein the applicator includes, between the cavity and an application surface to be brought into contact with the area to be treated, a wall with a smallest thickness ($e_{min}$) between 0.1 mm and 50 mm.

10. The assembly according to claim 9, wherein $e_{min}$ is 0.5 mm.

11. The assembly according to claim 1, wherein the cavity includes a non-constant thickness wall.

12. The assembly according to claim 1, wherein the cavity is hermetically sealed.

13. The assembly according to claim 1, wherein the applicator includes a non-metallic material of density greater than or equal to 1.5 g/cm³ comprising the application surface and configured to come into contact with the area to be treated.

14. The assembly according to claim 13, wherein the non-metallic material is stone or glass.

15. The assembly according to claim 14, wherein the applicator includes a heat conductive material comprising at least a portion of an application surface configured to come into contact with the area to be treated, the heat conductive material having a thermal conductivity greater than or equal to 1 $Wm^{-1}K^{-1}$.

16. The assembly according to claim 15, wherein the heat conductive material has a thermal conductivity of at least 40 $Wm^{-1}K^{-1}$.

17. The assembly according to claim 15, wherein the applicator includes a material of specific heat capacity greater than or equal to 500 $J\ kg^{-1}K^{-1}$.

18. The assembly according to claim 17, wherein the specific heat capacity is greater than or equal to 1000 J kg$^{-1}$K$^{-1}$.

19. The assembly according to claim 18, wherein the specific heat capacity is greater than or equal to 2000 J kg$^{-1}$K$^{-1}$.

20. The assembly according to claim 1, wherein a portion of the application surface configured to come into contact with the area to be treated includes a material with a thermal conductivity greater than or equal to 1 Wm$^{-1}$K$^{-1}$.

21. The assembly according to claim 20, wherein the thermal conductivity of the material is at least 40 Wm$^{-1}$K$^{-1}$.

22. The assembly according to claim 1, wherein the applicator includes a material of specific heat capacity greater than or equal to 500 J kg$^{-1}$K$^{-1}$.

23. The assembly according to claim 22, wherein the specific heat capacity is greater than or equal to 1000 J kg$^{-1}$K$^{-1}$.

24. The assembly according to claim 23, wherein the specific heat capacity is greater than or equal to 2000 J kg$^{-1}$K$^{-1}$.

25. The assembly according to claim 1, wherein the application surface includes a material having a thermal inertia greater than or equal to 1,000 Jm$^{-2}$ K$^{-1}$ s$^{-1/2}$.

26. The assembly according to claim 25, wherein the thermal inertia of the material is greater than or equal to 5,000 Jm$^{-2}$ K$^{-1}$ s$^{-1/2}$.

27. The assembly according to claim 26, wherein the thermal inertia of the material is greater than or equal to 10,000 Jm$^{-2}$ K$^{-1}$ s$^{-1/2}$.

28. The assembly according to claim 1, wherein the applicator has a mass greater than or equal to 15 g.

29. The assembly according to claim 1, wherein the applicator includes a grasping surface including an insulating material with a thermal conductivity less than or equal to 1 Wm$^{-1}$K$^{-1}$.

30. The assembly according to claim 29, wherein the thermal conductivity is less than or equal to 0.5 Wm$^{-1}$K$^{-1}$.

31. The assembly according to claim 30, wherein the thermal conductivity is less than or equal to 0.1 Wm$^{-1}$K$^{-1}$.

32. The assembly according to claim 1, further comprising a container.

33. The assembly according to claim 32, wherein the applicator and the container are contained in a common packaging device.

34. The assembly according to claim 32, wherein the applicator is detachably connected to the container.

35. The assembly according to claim 1, further comprising a substrate.

36. The assembly according to claim 35, wherein the substrate is detachably fixed on the applicator.

37. The assembly according to claim 1, wherein the applicator is at least partially magnetic.

38. An assembly including:
a non-rotatable applicator including
an application surface configured to treat an area of skin, and
at least one material with thermal properties such that, when the at least one material is heated to a temperature above 30° C. and which temperature does not cause thermal damage to the skin when the application surface is contacted with the skin for 15 seconds, the application surface maintains, after this application, a temperature above or equal to 30° C.,
wherein the applicator includes a flexible lip configured to come into contact with the area of skin to be treated.

39. The assembly according to claim 1, wherein the applicator includes a detachable vibrator.

40. The assembly according to claim 1, wherein the applicator includes a detachable electrode connected to a power source.

41. The assembly according to claim 1, wherein the applicator includes an application surface including a detachable part.

42. An assembly including:
a non-rotatable applicator including
an application surface configured to treat an area of skin, and
at least one material with thermal properties such that, when the at least one material is heated to a temperature above 30° C. and which temperature does not cause thermal damage to the skin when the application surface is contacted with the skin for 15 seconds, the application surface maintains, after this application, a temperature above or equal to 30° C.,
wherein the applicator includes an application surface including a detachable part, and
wherein the detachable part includes an absorbent material.

43. The assembly according to claim 1, wherein the applicator is configured to retain, at the application surface, a temperature above or equal to 30° C. for a retention time of at least 30 seconds after being heated to 50° C. and applied to the skin.

44. The assembly according to claim 43, wherein the retention time is at least 1 minute.

45. The assembly according to claim 44, wherein the retention time is at least 15 minutes.

46. The assembly according to claim 45, wherein the retention time is at least 30 minutes.

47. The assembly according to claim 1, wherein the applicator does not include compounds reacting together by an exothermic reaction.

48. The assembly according to claim 1, wherein the applicator is devoid of a power source or means of connection to a power source.

49. The assembly according to claim 1, further comprising a safety capsule configured to receive the applicator when the applicator is placed in a microwave oven.

50. The assembly according to claim 1, wherein the applicator includes a thermochromic indicator.

51. The assembly according to claim 1, wherein the application surface includes a first application surface and a second application surface, and the first application surface has a different shape from the second application surface.

52. An assembly including:
a non-rotatable applicator including
an application surface configured to treat an area of skin, and
at least one material with thermal properties such that, when the at least one material is heated to a temperature above 30° C. and which temperature does not cause thermal damage to the skin when the application surface is contacted with the skin for 15 seconds, the application surface maintains, after this application, a temperature above or equal to 30° C.,
wherein the applicator is U-shaped, and first and second application surfaces are disposed on different legs of the U-shaped applicator.

53. The assembly according to claim 1, wherein the compound is movable within the cavity, and the application surface includes a flat portion such that the applicator is configured to rest on the flat portion and the compound moves into contact with a back surface of the flat portion when the applicator is positioned to rest on the flat portion.

54. The assembly according to claim 1, wherein the applicator is shaped in the form of an annulus.

55. The assembly according to claim 54, wherein the applicator includes an internal channel passing through a center of the annulus, and the assembly includes a pump configured to dispense a composition through the internal channel.

56. The assembly according to claim 55, including a container,
wherein the pump includes an actuator coupled to the applicator such that movement of the applicator relative to the container actuates the actuator and dispenses the composition through the internal channel.

57. The assembly according to claim 1, wherein the applicator includes projections extending away from the application surface.

58. The assembly according to claim 57, wherein the projections are disposed on a detachable part configured to couple to the applicator.

59. An applicator including:
a non-rotary application surface including a material with a thermal conductivity greater than or equal to 1 $Wm^{-1}K^{-1}$;
a grasping surface including a material with a thermal conductivity less than or equal to 1 $Wm^{-1}K^{-1}$; and
a cavity inside the applicator containing at least 0.2 ml of a compound which changes state at a temperature between 30° C. and 80° C.

60. The applicator according to claim 59, wherein the non-rotary application surface includes a material with a thermal conductivity greater than or equal to 40 $Wm^{-1}K^{-1}$.

61. The applicator according to claim 59, wherein the grasping surface includes a material with a thermal conductivity less than or equal to 0.5 $Wm^{-1}K^{-1}$.

62. The applicator according to claim 61, wherein the grasping surface includes a material with a thermal conductivity less than or equal to 0.1 $Wm^{-1}K^{-1}$.

63. The applicator according to claim 59, wherein the application surface and the grasping surface are two parts assembled one on the other.

* * * * *